United States Patent [19]

Nawash et al.

[11] 4,315,513
[45] Feb. 16, 1982

[54] GASTROSTOMY AND OTHER PERCUTANEOUS TRANSPORT TUBES

[76] Inventors: Michael S. Nawash, 605 Nakoma St., Midland, Mich. 48640; Suzanne Stillman, 826 N. Whittier Dr., Beverly Hills, Calif. 90210; Robert S. Mason, 745 W. Mariposa Ave., El Segundo, Calif. 90245

[21] Appl. No.: 129,089

[22] Filed: Mar. 10, 1980

[51] Int. Cl.³ ..................... A61M 25/00; A61M 3/00
[52] U.S. Cl. .................................. 128/348; 128/242; 128/245
[58] Field of Search ................... 128/348, 347, 350 R, 128/239, 242, 243, 245, 349 R, DIG. 9, DIG. 16, DIG. 26, 303 R, 349 BV, 248

[56] References Cited

U.S. PATENT DOCUMENTS

| 2,649,092 | 8/1953 | Wallace | 128/243 |
|---|---|---|---|
| 3,253,594 | 5/1966 | Matthews et al. | 128/348 |
| 3,915,171 | 10/1975 | Shermeta | 128/348 |
| 3,961,632 | 6/1976 | Moossun | 128/347 |
| 3,982,544 | 9/1976 | Dyck | 128/349 R |
| 4,043,338 | 8/1977 | Homm et al. | 128/243 |

Primary Examiner—Robert Peshock
Assistant Examiner—Michael J. Foycik
Attorney, Agent, or Firm—Spensley, Horn, Jubas & Lubitz

[57] ABSTRACT

An improved gastrostomy or like percutaneous transport tube includes, at the end exterior to the abdominal wall, a nutrient supply coupling assembly including a mechanically simple one-way valve. A threaded cap closes the assembly, and may be replaced by a coupling member having a fitting for disconnectable attachment to a nutrient or other fluid supply. A tool is provided for preventing rotation of the assembly during removal and replacement of the cap and coupling member.

The assembly body includes a flange that extends parallel to the exterior abdominal wall. An annular skin protector disc seats between the flange and the abdominal wall, and includes spaced ridges arranged to permit the entry of air between the disc and the skin.

In another gastrostomy tube embodiment, an enlargement at the end emplaced in the stomach is of dome shape and acts as a one-way valve. A slit across the enlargement divides the dome into two sections. Nutrient fed through the tube to the dome interior forces open the sections to permit nutrient flow into the stomach. The pressure of fluid from the stomach against the exterior of the dome forces the two sections to seal the slit, preventing backflow through the tube.

Emplacement of a percutaneous transport tube is simplified by compressing the enlarged end (which is to be inserted into the stomach or other bodily region) into a capsule or binding of a material that dissolves in the body. The bound or encapsulated tube end then is insertable through a gastrostomy or like opening without the use of a stylet.

2 Claims, 10 Drawing Figures

U.S. Patent Feb. 16, 1982 Sheet 2 of 2 4,315,513
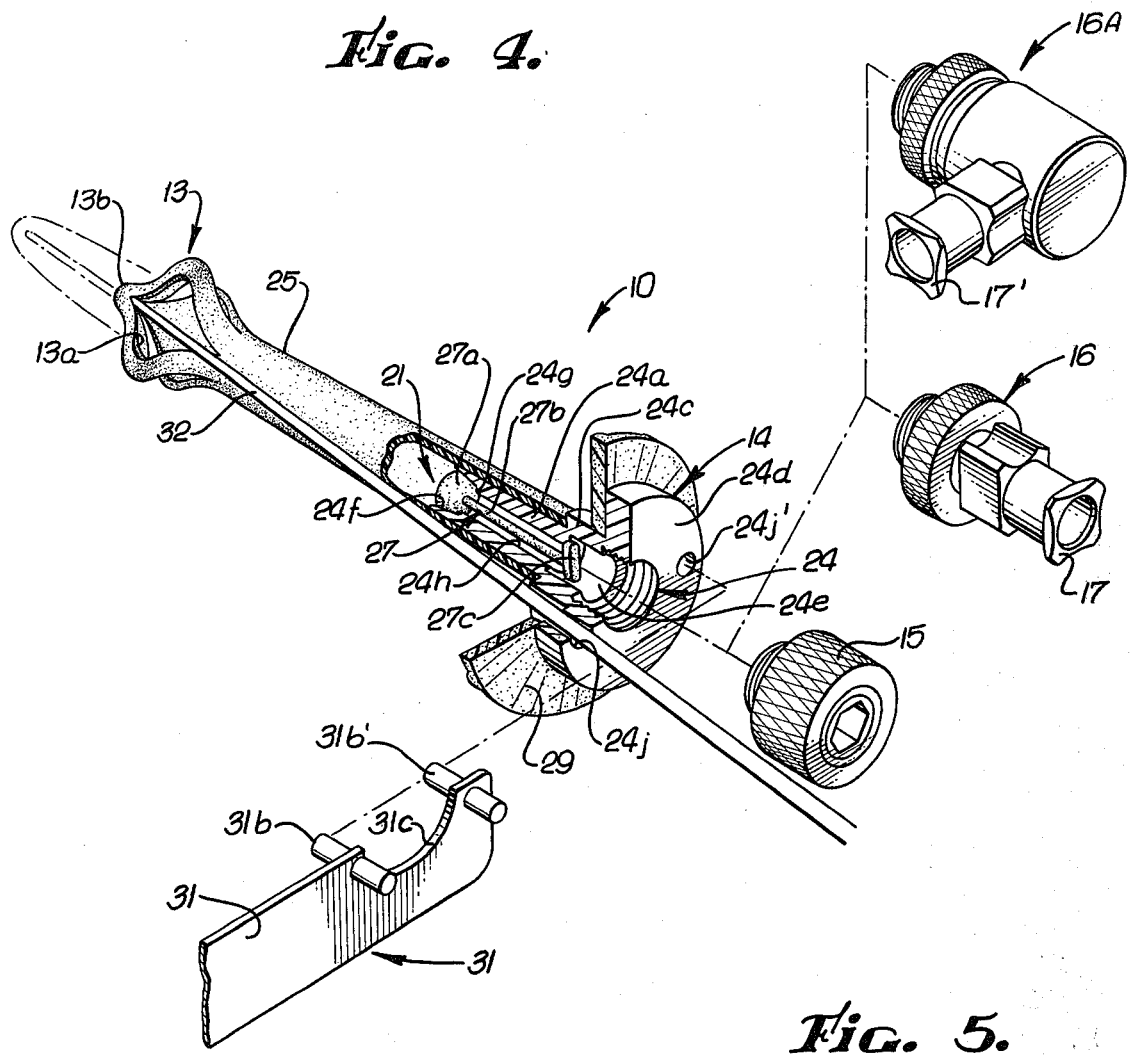
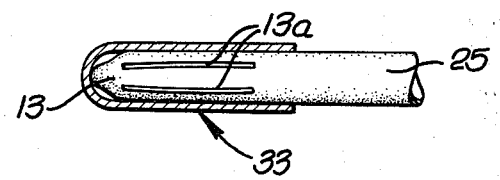
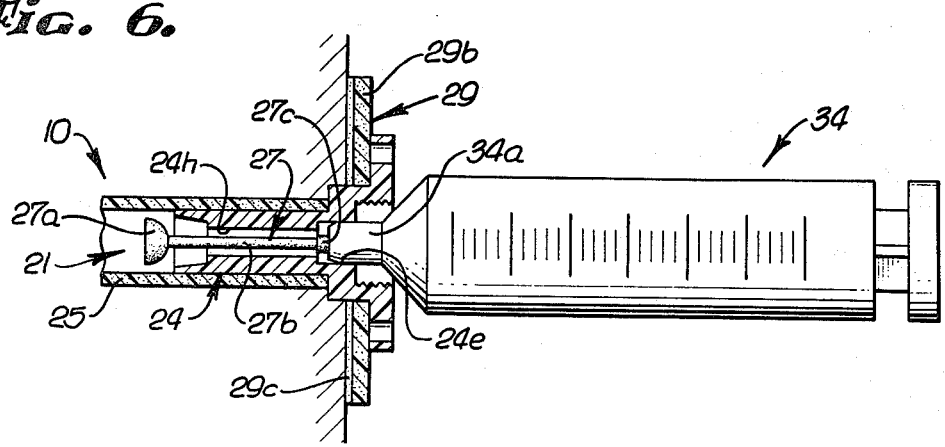

GASTROSTOMY AND OTHER PERCUTANEOUS TRANSPORT TUBES

BACKGROUND OF THE INVENTION

1. Field of the Invention

The present invention relates to improved gastrostomy and other percutaneous tubes, and to one-way valves and insertion techniques useful with such tubes.

2. Description of the Prior Art

Certain medical conditions require the continuous or repeated percutaneous introduction to bodily organs or tissues of substances such as nutrients (e.g., glucose) or drugs. This may be accomplished by an appropriate percutaneous transport tube. An example of such a condition is a glycogen storage deficiency which requires the delivery of carbohydrates directly into the stomach. For this purpose a surgical opening ("gastrostomy") is made through the abdominal wall into the stomach. A percutaneous transport tube, referred to as a "gastrostomy tube", is inserted through the opening and used to supply glucose solution solution or other nutrient directly into the stomach.

A typical prior art gastrostomy tube is on the order of 25 centimeters long and consists of a flexible tubing section, typically 5 to 8 millimeters in diameter, made of a silicone composition that is medically inert. The end which is inserted into the stomach may have a Malecot tip consisting of three or four generally semicircular loops of material which radiate from the end of the tube and join at a tip. The radial loop sections can seat against the interior stomach wall so as to impede the inadvertent withdrawal of the tube. Liquid nutrient passes from the tube into the stomach through the openings between these semicircular loops.

The other end of the tube, which is external to the body, is provided with an enlarged diameter end section for connection to a pump that forces the nutrient through the tube. When nutrient is not being administered, the extending tube section is clamped with a rubber band or mechanical clamp to prevent the outflow of gasses or liquids from the stomach due to the buildup of pressure in the stomach.

Other percutaneous transport tubes are of generally similar design, including a tube of suitable material such as silicone with appropriate retention mechanisms at one or both ends. A number of problems are inherent in such prior gastrostomy or like percutaneous transport tubes. First, a relatively long section of the tube extends outside of the abdominal wall. This is unsightly and uncomfortable. One object of the present invention is to provide a percutaneous transport tube having an outer end which is generally flush with the external abdominal wall.

Another disadvantage is the requirement for clamping a gastrostomy or like tube to prevent the backflow of liquid or gas from the stomach. A further object of the present invention is to provide percutaneous transport tubes include one-way valves which prevent such backflow without the necessity for external clamping. Alternatively, for certain purposes one-way outflow from the body may be required, and the valve may be oriented to permit such outflow.

Another problem is the manner in which the pump is attached to a gastrostomy tube. To simplify such connection, it is an object of the present invention to provide a percutaneous transport tube having an easy to use connector assembly for facilitating pump interconnection. Yet another objective is to provide a connector arrangement which permits the direct insertion of nutrient fluids from a syringe assembly for use in an emergency situation when a fluid pump is not available.

A further shortcoming of the prior art concerns the manner of insertion of a gastrostomy tube into the stomach. Typically this is accomplished by a surgeon who inserts a stylet through the length of the tube and up against the end of the Malecot tip. As the surgeon pushes the stylet and tube through the abdominal wall opening, the force of the end of the stylet elongates the Malecot tip, thereby pulling the semicircular sections into a straight, elongated configuration. When so elongated, the Malecot tip can pass through a small gastrostomy opening into the stomach. When the stylus then is withdrawn, the resiliency of the tube material pulls the elongated sections of the Malecot tip back into semicircular configuration, thereby securing the end within the stomach.

A further object of the present invention is to provide simplified means for gastrostomy or like tube insertion. One such objective is to encapsulate or surround the Malecot or other tip configuration in a capsule or binding of material which dissolves within the stomach. Such arrangement permits percutaneous transport tube insertion without the use of a stylus, thereby simplifying the emplacement procedure.

Some improvements in gastrostomy tubes and stomach intubation and catheter placement systems are known in the prior art. For example, U.S. Pat. No. 3,915,171 to Shermata discloses a gastrostomy tube that uses a pair of retention bulbs which respectively engage the inner stomach wall and the outer abdominal wall. The inner bulb is stiffly flexible, and can be collapsed by a stylet for insertion through a stab wound in the stomach.

The U.S. Pat. No. 3,961,632 to Moossun shows a plastic tube catheter which is placed through the abdomen and stomach walls using a central steel needle that is withdrawn from the plastic tube after insertion. An annular section of the plastic tube is inflated with air to form an interior balloon structure within the stomach. A locking disc is clamped around the plastic tube on the outside of the abdomen wall to maintain the catheter in place.

The U.S. Pat. No. 3,253,594 to Matthews et al. discloses a peritoneal cannula which uses an annular balloon arrangement to retain the inner end of the cannula in place against the flesh. On the outside of the body, a flange or disc is held against the skin by a threaded locking cap, the position of which can be adjusted axially along the cannula.

The British Pat. No. 1,131,436 to Chirana Zavady Zdravotnicke Techniky discloses a gastrostomy apparatus in which the head at the external end of a tubular body is provided with a tripartite rubber flap valve secured in place by a threaded ring. The tubular body is closed by means of a stopper made of a water-repellent non-toxic material.

The U.S.S.R. Pat. No. 286,138 discloses a stomach fistular pipe having a normally closed valve which is opened by a shaft that extends through the pipe and through the body wall.

None of these patented devices satisfy the above described objectives of the present invention.

SUMMARY OF THE INVENTION

The objectives are achieved by the inventive gastrostomy and other percutaneous transport tubes, one feature of which is an exterior assembly which rests flush against the outside abdominal wall. Unsightly and inconvenient external tube extensions are eliminated. Mounted within the assembly is a one-way valve that prevents the backflow of fluids or gas from the stomach. Clamping of a tube extension is eliminated.

The external assembly also includes a replaceable connector arrangement which simplifies attachment to the nutrient pump. A screw threaded cap is easily removed and replaced by a conventional snap-together tubular coupling. This simplifies hook-up of the pump. In an emergency, the threaded cap or interconnection fixture may be removed and nutrient forced directly into the gastrostomy or like tube using a syringe.

A skin protector disc spaces the external assembly at a slight distance from the abdominal wall so as to allow air to reach the underlying skin, thereby reducing the likelihood of adverse side effects from direct contact of the external assembly with the skin.

To simplify insertion of a percutaneous transport tube into the stomach or other bodily organ or region, a soluble capsule or binding is disclosed which surrounds a Malecot or like tip. This retains the tip in narrow, elongated form for simple insertion without the need of a stylet. Once emplaced, bodily fluids dissolve the capsule or binding, and the resilient tip assumes its outwardly bulged configuration that retards inadvertent removal of the tube.

In another embodiment, a gastrostomy tube is provided with a internal, resilient enlarged head which is configured itself to function as a one-way valve. This arrangement thus functions both to retain the tube end within the stomach and to prevent the backflow of stomach fluids.

BRIEF DESCRIPTION OF THE DRAWINGS

A detailed description of the invention will be made with reference to the accompanying drawings wherein like numerals designate corresponding elements in the several figures, which are not necessarily to scale.

FIG. 4 is an exploded pictorial view, partly broken away and in section, showing one method for installing the gastrostomy tube of FIG. 2, and also showing alternative pump connectors useful with the gastrostomy tube and a tool for aiding in the attachment of such connectors.

FIG. 5 illustrates an inventive soluble capsule assembly for facilitating the insertion of the gastrostomy tube of FIG. 2 without the use of a stylet.

FIG. 6 is a pictorial view, partly in section, showing the use of syringe to supply the nutrient.

DESCRIPTION OF THE PREFERRED EMBODIMENTS

The following detailed description is of the best contemplated modes of carrying out the invention. This description is not to be taken in a limiting sense, but is made merely for the purpose of illustrating the general principles of the invention, since the scope of the invention best is defined by the appended claims. Operational characteristics attributed to forms of the invention first described shall be attributed to forms later described, unless such characteristics obviously are inapplicable or unless specific exception is made.

In the following description, the inventive percutaneous transport tubes are illustrated by way of gastrostomy tube embodiments. However, the invention is not so limited, but comprehends other percutaneous transport tubes of like characteristics.

Figure 1:
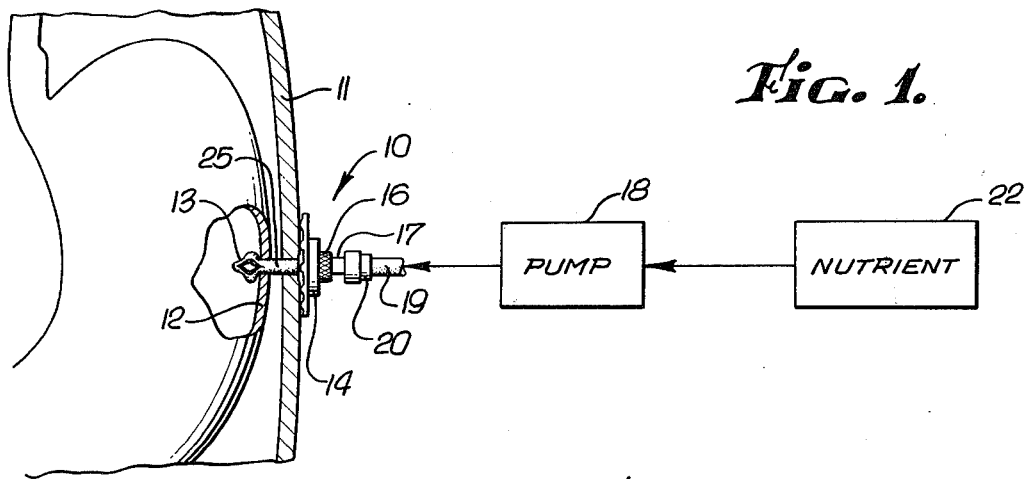
FIG. 1 is a diagrammatic view of one embodiment of the inventive gastrostomy or like percutaneous transport tube emplaced in a patient and in use for the supply of nutrient.

Referring to FIG. 1, the inventive percutaneous transport tubes are typified by a gastrostomy tube 10 which extends through the abdominal wall 11 and stomach wall 12 of the patient. A Malecot tip 13 retains the tube in the stomach, while the external portion of the tube consists of an assembly 14 that rests generally flush with the outside abdominal wall.

As described below in conjunction with FIGS. 2 and 4, a cap 15 is removed from the assembly 10 and replaced by a fitting 16 provided with a "Lur-lok" or other connector 17 to facilitate attachment to a nutrient pump 18. As shown in FIG. 1, the pump 18 is connected to the gastrostomy tube 10 via a hose 19 and a coupling 20 that mates with the connector 17. Glucose or other nutrient then is pumped from a source 21 into the patient's stomach via the pump 18, the hose 19, and the inventive gastrostomy tube 10.

When nutrient delivery is complete, the coupling 20 is disconnected. The fitting 16 may be left in place, or may be removed and replaced by the cap 15. In either event, a one-way valve 21 contained within the assembly 14 prevents the backflow or outward leakage of liquid or gas from the stomach.

Figures 2, 2A:
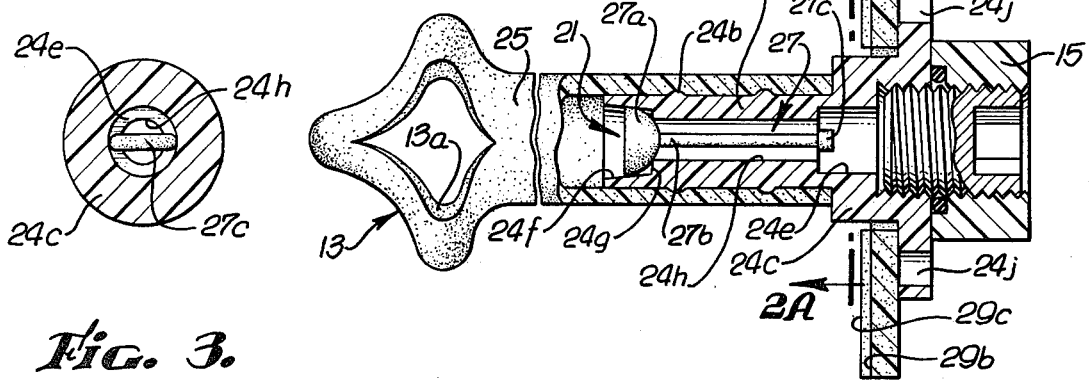
FIG. 2 is a transverse sectional view of the gastrostomy tube of FIG. 1.
FIG. 2A is a sectional view of a portion of the one-way valve included in the gastrostomy tube of FIG. 2, as viewed along the line 2A—2A thereof.
Figure 3:
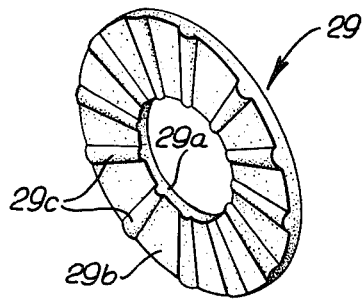
FIG. 3 is a perspective view of the skin protector disc used with the gastrostomy tube of FIG. 2.

As shown in FIGS. 2, 3 and 4, the external assembly 14 includes a rigid, generally cylindrical body 24 that may be formed of nylon or like inert plastic material. The body 24 includes a cylindrical forward projection 24a which is matingly inserted into an end of a flexible tube 25 that may be formed of silicone. The exterior surface of the projection 24a may be provided with circumferential ridges 24b to aid in gripping the tube 25. Alternatively or additionally, an adhesive may be used to bond the projection 24a to the inside of the tube 25.

The body 24 also includes a central shoulder portion 24c and an outer flange 24d which contain an axial counterbore 24e. The distal end of the projection 24a contains a conically tapered counterbore 24f the bottom of which forms a shoulder 24g surrounding the interior channel 24h through the body 24. The shoulder 24g serves as the seat for the one-way valve 21.

The closure for the one-way valve 21 is the hemispherical end 27a of a valve member 27 that is formed of a soft silicone elastomer. This member 27 includes an elongated stem 27b that extends through the channel 24h from the valve closure 27a to a crosspiece 27c situate within the counterbore 24e. The length of the stem 27b is sufficient to permit limited axial movement of the valve member 27 within the body 24.

When a back pressure condition exists within the stomach, the pressure of gas or liquid entering the tube 25 through the Malecot tip 13 forces the valve closure 27a into flow-impeding contact with the shoulder 24g (as shown in FIG. 2). This closes the one-way valve 26, and inhibits the outward flow or leakage of stomach gas or fluid through the gastrostomy tube 10. On the other hand, when nutrient is being pumped into the stomach, (as shown in FIG. 1) this nutrient will flow past the crosspiece 27c into the channel 24h and will force the valve closure 27a away from the shoulder 24g. Unimpeded nutrient flow into the stomach thus is facilitated past the now open valve 21. For other uses, a percutaneous transport tube in accordance with the present invention may be provided with a one-way valve which prevents the outflow of fluids from the body.

To protect the skin from abrasion of the flange 24d and to permit the contact of air with the abdominal wall exterior beneath the assembly 14, a skin protector disc 29 (FIGS. 2 and 3) is employed. This protector disc 29 advantageously is formed of a flexible, non-allergetic, medically inert synthetic plastic such as the silastic silicone composition sold commercially by Dow-Corning Corporation as Type MDX 44-210. The protector disc 29 is annular in shape and has a central aperture 29a which surrounds the shoulder portion 24c of the body 24. The disc 29 thus is situated between the flange 24d and the exterior of the abdominal wall 11. The disc surface 29b which faces the abdominal wall is provided with a set of raised ridged 29c advantageously arranged in spoke-like fashion. The ridges 29c maintain the disc face 29b slightly spaced away from the abdominal wall skin so as to permit the entry of air between the skin and the disc 29. The resultant air exposure reduces the likelihood of adverse skin effects that might otherwise possibly occur if the entire assembly 14 were in direct contact with the skin.

To connect the nutrient pump 18 to the gastrostomy tube 10, the cap 15 is removed and a fitting 16 (FIG. 4) is threaded into the body 24. To prevent rotation of the body 24, the tool 31 shown in FIG. 4 may be used. It includes a rigid handle 31a at one end of which are attached two spaced pins 31b, 31b'. These are inserted into corresponding holes 24j, 24j' in the flange 24d. A recess 31c is provided in the tool 31 between the pins 31b, 31b' to provide clearance for the cap 15 or the fitting 16.

With the tool 31 engaging the body 24, a hex-hand wrench may be used to remove the cap 15 for replacement by a fitting 16. In FIGS. 2 and 4, the cap 15 is configured to receive a hex-head wrench. However, it may be more convenient to provide a slot on the cap 15 so that it may be removed with a screwdriver or a coin. Use of the tool 31 prevents rotation of the body 24, thereby preventing abrasion of the skin which might otherwise occur.

The fitting 16A shown in FIG. 4 has a swivel design so that the connctor 17' extends at right angles from the axis of the body 24. This arrangement is useful when the patient is prone so that the nutrient supply hose 19 can extend along the patient's body.

FIG. 4 also illustrates one method for emplacing the gastrostomy in a patient's body. The surgeon first forms an appropriate opening through the abdominal wall and stomach wall. He then places a stylet 32 through one of the holes 24j, through the opening 29a in the skin protector disc 29 (which itself may be pulled back to permit this insertion), along the tube 25 and through one of the apertures 13a of the Malecot tip 13 into the forward section 13b thereof. Forward pressure of the stylet collapses the Malecot tip to the position shown in phantom in FIG. 4. Insertion is facilitated. When the tip 13 is inside the stomach, the stylet 32 is removed. The resiliency of the tubing material then causes the tip 13 to bulb outward, completely the installation. Fluid flow from the tube 25 takes place through the apertures 13a.

A much simpler installation technique is illustrated in FIG. 5. Here, in accordance with another aspect of the present invention, the Malecot tip 13 is elongated and compressed into a capsule 33 made of gelatin or other material which will dissolve in bodily fluids within the stomach. The gastrostomy tube may come prepackaged in this manner. Then, it can emplaced within the patient by direct insertion through the gastrostomy opening. When the capsule 33 dissolves, the resiliency of the tube material will force the tip 13 to bulge out into its expanded condition.

In an emergency situation where no pump 18 is available, glucose or other nutrient solution may be supplied to the patient directly through the gastrostomy tube 10, for example, by using a syringe (without a needle) 34 as illustrated in FIG. 6. To this end, the cap 15 is removed, and the cylindrical tip 34a of the syringe 34 is inserted into the counterbore 24e. Advantageously, this counterbore 24e is dimensioned both in diameter and length so as to receive the tip of a conventional syringe, without having the tip interfere with the crosspiece 27c of the valve member 27. As the plunger of the syringe 34 is depressed, the force of the ingoing fluid will of course open the one-way valve 21, permitting the nutrient to flow into the stomach. However, if the crosspiece 27c of the valve 27 should interfere with such flow, the person administering the nutrient could take a needle or wire and push the valve member 27 through the channel 24h and tube 25 directly into the stomach. The member 27 would then be passed through the patient's alimentary canal without adverse effect. With the member 27 removed, an open flow path is provided through the gastrostomy tube 10 to facilitate emergency supply of the nutrient. Replacement of the cap 15 then would prevent backflow from the stomach.

Figure 7:
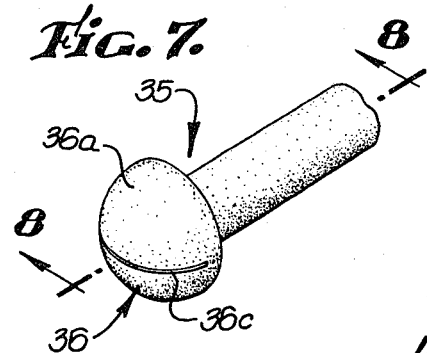
FIG. 7 is a pictorial of another gastrostomy tube in accordance with the present invention.
Figure 8:
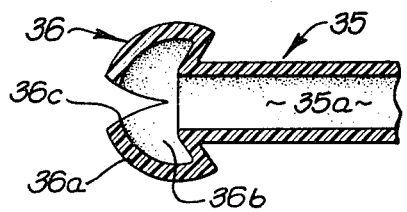
FIG. 8 is a partial transverse sectional view of the gastrostomy tube of FIG. 7 illustrating the one-way valve operation of the end of the tube which is inserted into the stomach.

An alternative gastrostomy tube 35 is illustrated in FIGS. 7 and 8. There, the external end (not shown) of the tube would not be provided with a one-way valve, since the interior end 36 itself functions as such a one-way valve.

In particular, the tube 35 including the end 36 is formed of a flexible, resilient, medically inert plastic material such as silicone. The end 36 is generally mushroon-shaped, and includes a dome portion 36a, the interior 36b of which is hollow, and which has a transverse slit 36c across the end thereof. The slot 36c divides the dome 36a into two sections. When nutrient fluid is pumped into the patient, it flows through the tube interior 35a and forces the two sections of the dome 36a to spread apart at the slit 36c, as shown in FIG. 8. This results in an opening through which the fluid can enter the stomach. When nutrient delivery is complete, the resliency of the tubular material causes the dome 36a to revert back to the closed condition shown in FIG. 7. Fluid or gas pressure within the stomach forces the dome 36a to remain in this "closed" state, forcing together the slit 36c in the manner of a lip seal. Backflow is prevented.

Figure 9:
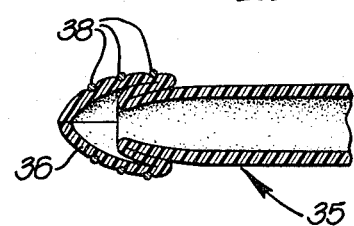
FIG. 9 is a sectional view of a soluble binding arrangement for facilitating the insertion of a gastrostomy tube without the use of a stylet.

The gastrostomy tube 35 of FIGS. 7 and 8 may be packaged for insertion using the gelatin capsule technique illustrated in FIG. 5. Alternatively, the head 36 may be compressed and wrapped or bound in a soluble sutre thread 38 or other web or thread made of a material which is soluble in the stomach. The same soluble thread wrapping technique shown in FIG. 9 may be used with a gastrostomy tube of other configuration (such as the tube 10 of FIG. 2) having a Malecot or mushroom-shaped tip.

We claim:

1. In a gastrostomy or like percutaneous transport tube of the type having a length of tubing with a first end configured for enlargement when inserted into the stomach or other bodily region of a patient, said first end having apertures for the passage of fluid, a one-way valve and fluid supply coupling assembly at the other end of said tubing, comprising:

a rigid, generally cylindrical body having at one end a projection engaging said tubing, there being an axial channel through said projection, said body having at the other end a flange adapted to extend in closely spaced parallel relationship to the exterior abdomeninal wall then said percutaneous transport tube is emplaced, connector means, exteriorly removably attachable to said body at the flange end thereof, for disconnectable coupling to a nutrient or like fluid supply, and a one-way valve in said body comprising:

a tapered counterbore extending coaxially from the distal end of said projection to said axial channel, a second counterbore extending coaxially through said flange end to said channel, and a flexible resilient unitary valve member consisting of an elongated stem extending through said channel, a valve closure at one end of said stem, said valve closure being disposed within said tapered counterbore, and a crosspiece at the other end of said stem, said crosspiece being disposed within said second counterbore, said stem being slightly longer than said channel so as to permit limited axial movement of said unitary valve member from a closed position in which back pressure from said bodily region forces said valve closure into valve closing relationship with the shoulder between said tapered counterbore and said channel, and an open position in which nutrient or like fluid from said supply passing through said channel urges said valve closure away from said shoulder so as to permit the flow of said fluid into said bodily region.

2. In a gastrostomy or like percutaneous transport tube of the type having a length of tubing with a first end configured for enlargement when inserted into the stomach or other bodily region of a patient, and apertured for the passage of fluids, an assembly at the other end of said tubing, comprising:

a rigid, generally cylindrical member having a central shoulder portion, having at one end an axial projection engaging said tubing, and having at the other end a radially extending flange, there being an axial passageway through said member and communicating with said tubing, and an -annular skin protector disc formed of resilient material, said disc having a central aperture through which said shoulder portion extends, said disc thus seating between said flange and the external skin of the abdominal wall when said percutaneous transport tube is emplaced in a patient, said skin protector disc having a set of raised ridges integral therewith on the side facing said skin, said ridges being arranged so as to permit the entry of air between said disc and the exterior abdominal wall, and a one-way valve disposed in said cylindrical member and operative to enable the flow of fluids in one direction only through said assembly, comprising:

a first counterbore extending coaxially from the distal end of said axial projection to said passageway, a second counterbore extending coaxially through said flange to said passageway, and a flexible resilient unitary valve member consisting of an elongated stem extending through said passageway, a valve closure on one end of said stem, said valve closure being disposed within one of said counterbores, and a crosspiece at the other end of said stem, said crosspiece being disposed within the other of said counterbores, said stem being slightly longer than said passageway so as to permit limited axial movement of said unitary valve member from a closed position in which flow is prevented in one direction and an open position in which flow is permitted in the opposite direction.

* * * * *